United States Patent
Chen et al.

(10) Patent No.: US 11,407,692 B2
(45) Date of Patent: Aug. 9, 2022

(54) METHOD FOR OXIDATIVE CLEAVAGE OF COMPOUNDS WITH UNSATURATED DOUBLE BOND

(71) Applicant: NATIONAL TSING HUA UNIVERSITY, Hsinchu (TW)

(72) Inventors: Chien-Tien Chen, Hsinchu (TW); Yi-Ya Liao, Hsinchu (TW); Ya-Pei Chen, Hsinchu (TW)

(73) Assignee: NATIONAL TSING HUA UNIVERSITY, Hsinchu (TW)

( * ) Notice: Subject to any disclaimer, the term of this patent is extended or adjusted under 35 U.S.C. 154(b) by 0 days.

(21) Appl. No.: 16/860,690

(22) Filed: Apr. 28, 2020

(65) Prior Publication Data
US 2021/0206702 A1 Jul. 8, 2021

(30) Foreign Application Priority Data
Jan. 2, 2020 (TW) .................. 109100028

(51) Int. Cl.
| | |
|---|---|
| *C07B 41/04* | (2006.01) |
| *C07C 227/02* | (2006.01) |
| *C07D 413/06* | (2006.01) |
| *B01J 31/22* | (2006.01) |

(52) U.S. Cl.
CPC ............ *C07B 41/04* (2013.01); *B01J 31/226* (2013.01); *B01J 31/2217* (2013.01); *C07C 227/02* (2013.01); *C07D 413/06* (2013.01); *B01J 2231/70* (2013.01); *B01J 2531/56* (2013.01)

(58) Field of Classification Search
CPC ............ B01J 31/0201; B01J 31/0232; B01J 31/1835; B01J 31/2217; B01J 31/2226; B01J 31/2243; B01J 31/2256; B01J 31/226; C07C 201/12; C07C 227/02; C07C 413/06; C07C 205/45; C07B 41/04; C07D 413/06

See application file for complete search history.

(56) References Cited

PUBLICATIONS

Chen et al., ACS Catal., 2020, 10, pp. 3676-3683.*

\* cited by examiner

*Primary Examiner* — Alicia L Otton
(74) *Attorney, Agent, or Firm* — Muncy, Geissler, Olds & Lowe, P.C.

(57) ABSTRACT

A method for oxidative cleavage of a compound with an unsaturated double bond is provided. The method includes the steps of:
(A) providing a compound (I) with an unsaturated double bond, a trifluoromethyl-containing reagent, and a catalyst;

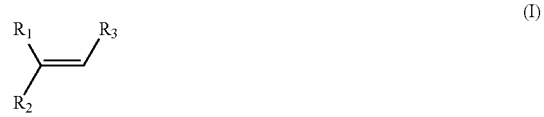

wherein, the catalyst is represented by Formula (II):

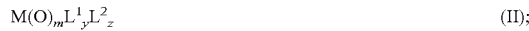

wherein, M, $L^1$, $L^2$, m, y, z, $R_1$, $R_2$ and $R_3$ are defined in the specification; and
(B) mixing the compound with an unsaturated double bond and the trifluoromethyl-containing reagent to perform an oxidative cleavage of the compound with the unsaturated double bond by using the catalyst in air or under oxygen atmosphere condition to obtain a compound represented by Formula (III):

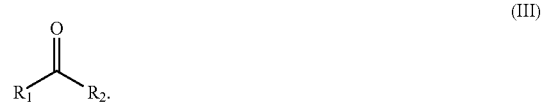

11 Claims, No Drawings

METHOD FOR OXIDATIVE CLEAVAGE OF COMPOUNDS WITH UNSATURATED DOUBLE BOND

CROSS REFERENCE TO RELATED APPLICATION

This application claims the benefits of the Taiwan Patent Application Serial Number 109100028, filed on Jan. 2, 2020, the subject matter of which is incorporated herein by reference.

BACKGROUND OF THE INVENTION

1. Field of the Invention

The present disclosure relates to a method of oxidative cleavage and, more particularly, to a method of oxidative cleavage for a compound with an unsaturated double bond under an aerobic condition to obtain a carbonyl compound.

2. Description of Related Art

Oxidative cleavage is one of the important reactions for a compound with an unsaturated double bond, such as olefins. Generally, olefins can be subjected to an oxidative cleavage reaction by (1) ozone; (2) high oxidation state metal oxides, such as potassium permanganate ($KMnO_4$), or osmium tetroxide ($OsO_4$); and (3) Pd/Cu catalysis.

However, due to the use of strong oxidants and peroxides for the reaction, the oxidative cleavage of olefins has the disadvantages of high cost and strict operating conditions, and it has difficulty in mass production. In addition, half of the oxidation products in the oxidative cleavage reaction is not the expected product in almost all cases, and it causes additional waste and environmental pollution.

Therefore, there is a strong and urgent demand to develop a method of oxidative cleavage for a compound with an unsaturated double bond to overcome the disadvantages of common oxidative cleavage and increase economic benefits.

SUMMARY OF THE INVENTION

In view of this, the present disclosure provides a method for oxidative cleavage of a compound with an unsaturated double bond. The method can be performed by using air or oxygen as an oxidant source under mild conditions, thereby overcoming the drawbacks of high cost or strict operating conditions with respect to conventional oxidative cleavage reactions. At the same time, the other half of the oxidation products are introduced with trifluoromethyl group, which greatly improves economic value.

The present disclosure provides a method for oxidative cleavage of a compound with an unsaturated double bond, comprising the steps of: (A) providing a compound (I) with an unsaturated double bond, a trifluoromethyl-containing reagent, and a catalyst;

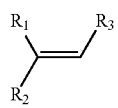
(I)

wherein, $R_1$ and $R_2$ are each independently H, $C_{1-20}$ alkyl, $C_{3-20}$ cycloalkyl, $C_{6-18}$ aryl, or $C_{4-18}$ heteroaryl, or $R_1$ and $R_2$ are fused to be $C_{6-18}$ aralkyl; $R_3$ is H, $C_{1-10}$ alkyl, $C_{3-10}$ cycloalkyl, $C_{6-10}$ aryl, or $C_{4-10}$ heteroaryl, with the proviso that $R_1$, $R_2$ and $R_3$ are not H at the same time; wherein the catalyst is represented by Formula (II):

$$M(O)_m L^1_y L^2_z \qquad (II)$$

wherein, M is a metal selected from the group consisting of IVB, VB, VIB, and actinides; $L^1$ and $L^2$ are each a ligand; m and y are integers greater than or equal to 1; and z is an integer greater than or equal to 0;

(B) mixing the compound with an unsaturated double bond and the trifluoromethyl-containing reagent to perform an oxidative cleavage of the compound with the unsaturated double bond by using the catalyst in air or under oxygen atmosphere condition to obtain a compound represented by Formula (III):

The compound (1) with an unsaturated double bond according to the present disclosure may be an olefin compound. In the compound (I) with an unsaturated double bond, $R_1$ and $R_2$ are each independently H, $C_{1-20}$ alkyl, $C_{3-20}$ cycloalkyl, $C_{6-18}$ aryl, or $C_{4-18}$ heteroaryl, or $R_1$ and $R_2$ are fused to be $C_{6-18}$ aralkyl; $R_3$ is H, $C_{1-10}$ alkyl, $C_{3-10}$ cycloalkyl, $C_{6-10}$ aryl, or $C_{4-10}$ heteroaryl. Preferably, $R_1$ and $R_2$ are each independently H, $C_{1-10}$ alkyl, $C_{3-10}$ cycloalkyl, $C_{6-14}$ aryl, or $C_{4-12}$ heteroaryl, or $R_1$ and $R_2$ are fused to be $C_{6-12}$ aralkyl; $R_3$ is H, $C_{1-6}$ alkyl, $C_{3-6}$ cycloalkyl, $C_{6-10}$ aryl, or $C_{4-10}$ heteroaryl. More preferably, $R_1$ and $R_2$ are each independently H, $C_{1-6}$ alkyl, $C_{3-6}$ cycloalkyl, $C_{6-14}$ aryl, or $C_{4-10}$ heteroaryl, or $R_1$ and $R_2$ are fused to be $C_{6-10}$ aralkyl; $R_3$ is H, $C_{1-6}$ alkyl, or $C_{3-6}$ cycloalkyl.

In addition, in the compound (I) with an unsaturated double bond, R, $R_2$ and $R_3$ are not H at the same time In the present disclosure, the catalyst may be represented by Formula (II). In the catalyst represented by Formula (II), $L^1$ is a ligand and preferably selected from the group consisting of OTf, OTs, $NTf_2$, halogen, $RC(O)CH_2C(O)R$, OAc, OC(O)R, $OC(O)CF_3$, OMe, OEt, O-iPr, and butyl, wherein R is alkyl (preferably $C_{1-6}$ alkyl, more preferably $C_{1-3}$ alkyl). Furthermore, $L^2$ is a ligand and preferably selected from the group consisting of Cl, $H_2O$, $CH_3OH$, EtOH, THF, $CH_3CN$,

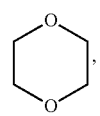

and ligand containing C=N unit.

In the present disclosure, the "ligand containing C=N unit" may comprise pyridine, oxazole, oxazoline, or imidazole. However, the present disclosure is not limited thereto. Specific example comprises 2,2'-bipyridyl, 3-chloropyridine, 2,6-dichloropyridine, 3,5-dichloropyridine, 2,6-di-tertbutylpyridine, 1-methylimidazole, 1,2-dimethylimidazole. However, the present disclosure is not limited thereto.

In one embodiment of the present disclosure, the "ligand containing C=N unit" may be represented by Formula (IV):

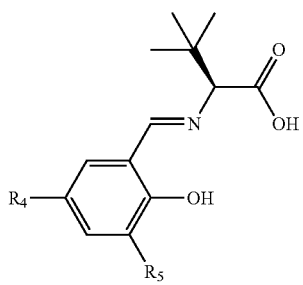

(IV)

wherein, $R_4$ and $R_5$ are each independently halogen, nitro, $C_{1-10}$ alkyl, $C_{6-18}$ aryl, or $C_{4-18}$ heteroaryl. Preferably, $R_4$ and $R_5$ may be each independently Cl, Br, $NO_2$ or $C_{1-10}$ alkyl.

In another embodiment, the "ligand containing C=N unit" may be represented by Formula (V):

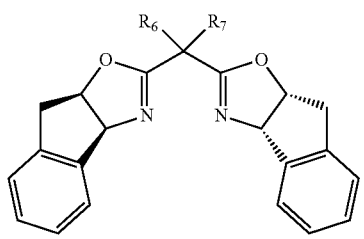

(V)

wherein $R_6$ and $R_7$ are each independently H, $C_{1-5}$ alkyl or $C_{3-4}$ cycloalkyl.

Further, in the catalyst represented by Formula (II), M may be a metal selected from the group consisting of IVB, VB, VIB, and actinides. In one aspect, M is a group IVB transition element, m is 1 and y is 2; wherein M may be Ti, Zr, or Hf. In another aspect, M is a group VB transition element, m is 1 and y is 2 or 3; wherein M may be V or Nb. In another aspect, M is a group VIB transition element, m is 1 and y is 4; wherein M may be Mo, W, or Cr. In another aspect, M is a group VIB transition element, m is 2 and y is 2; wherein M is Mo, W, or Cr. In yet another aspect, M is selected from the actinides, m is 2 and y is 2; wherein M is U.

In addition, in the catalyst of Formula (II), z may be an integer greater than or equal to 0. When z is 0, the specific example of the catalyst of Formula (II) may be $MoO_2Cl_2$, $V(O)Cl_3$, $V(O)O\text{-}iPr)_3$, $V(O)Cl_2$, $V(O)(OAc)_2$, $V(O)(O_2CCF_3)_2$, $Ti(O)(acac)_2$, $Zr(O)Cl_2$, $Hf(O)Cl_2$, $Nb(O)Cl_2$, $MoO_2(acac)_2$, $V(O)(OTs)_2$, $VO(OTf)_2$, or $V(O)(NTf_2)_2$. However, the present disclosure is not limited thereto. When z is an integer greater than 0, the specific example of the catalyst of Formula (II) may be any of formulas (II-1) to (II-4):

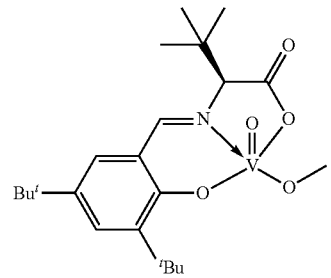

(II-1)

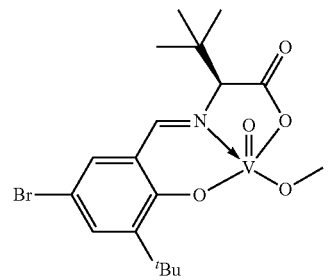

(II-2)

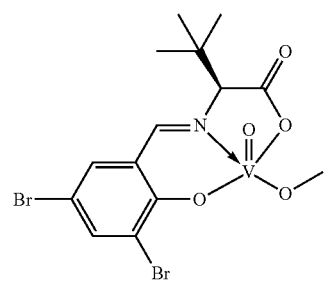

(II-3)

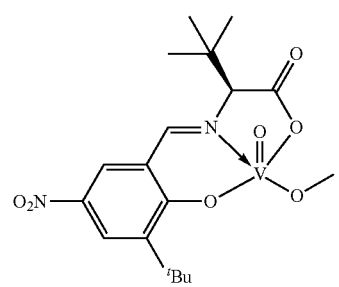

(II-4)

However, the present disclosure is not limited thereto.

The trifluoromethyl-containing reagent according to the present disclosure may be a monotrifluoromethyl- or perfluoroalkyl-containing reagent. The specific example comprises 3,3-Dimethyl-1-(trifluoromethyl)-1,2-benziodoxole, 3,3-Dimethyl-1-(perfluroalkyl)-1,2-benziodoxole, 3-oxo-1-(trifluoromethyl)-1,2-benziodoxole, 3-oxo-1-(perfluroalkyl)-1,2-benziodoxole, trifluomethyl dibenzothiophenium salts, perfluoroalkyl dibenzothiophenium salt, $CF_3SO_2Na$, and $CF_3(CF_2)_nSO_2Na$ (n=1-6). However, the present disclosure is not limited thereto.

In the compound represented by Formula (III), $R_1$ and $R_2$ are each independently H, $C_{1-20}$ alkyl, $C_{3-20}$ cycloalkyl, $C_{6-18}$ aryl, or $C_{4-18}$ heteroaryl, or $R_1$ and $R_2$ fused to be $C_{6-18}$ aralkyl group. Preferably, $R_1$ and $R_2$ are each independently H, $C_{1-10}$ alkyl, $C_{3-10}$ cycloalkyl, $C_{6-14}$ aryl, or $C_{4-12}$ heteroaryl, or $R_1$ and $R_2$ fuse to be $C_{6-12}$ aralkyl group. More preferably, $R_1$ and $R_2$ are each independently H, $C_{1-6}$ alkyl, $C_{3-6}$ cycloalkyl, $C_{6-12}$ aryl, or $C_{4-10}$ heteroaryl, or $R_1$ and $R_2$ fused to be $C_{6-10}$ aralkyl group. In one embodiment of the present disclosure, $R_1$ and $R_2$ are not H at the same time.

In the present disclosure, step (B) may further obtain a trifluoroketone- or trifluoroaldehyde-containing compound, trifluoroalkyl alcohol or a combination thereof.

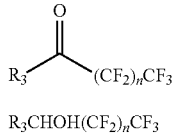
(VI)

$R_3CHOH(CF_2)_nCF_3$ (VII)

wherein $R_3$ is H, $C_{1-10}$ alkyl, $C_{3-10}$ cycloalkyl, $C_{6-10}$ aryl, or $C_{4-10}$ heteroaryl; n is an integer of 0 or 1 to 6.

In one embodiment of the present disclosure, $R_3$ is preferably H, $C_{1-6}$ alkyl, $C_{3-6}$ cycloalkyl, $C_{6-10}$ aryl, or $C_{4-10}$ heteroaryl; n is an integer of 0 or 1 to 3. More preferably, $R_3$ is preferably H, $C_{1-6}$ alkyl, or $C_{3-6}$ cycloalkyl; n is 0 or 1.

In another aspect of the present disclosure, the step (B) may further comprise adding an additive to the mixture of the compound with an unsaturated double bond and the trifluoromethyl-containing reagent, wherein the additive may be trimethylsilyl cyanide (TMSCN), anhydride or a combination thereof. However, the present disclosure is not limited thereto.

Herein, the term "alkyl" of the present disclosure includes unsubstituted alkyl or alkyl group substituted with halogen, nitro, alkenyl, cycloalkyl, alkoxy, aryl, or heteroaryl. The terms "cycloalkyl", "aryl", "heteroaryl" and "aralkyl" include unsubstituted groups or groups substituted with alkyl, halogen, nitro, alkenyl, cycloalkyl, alkoxy, aryl, or heteroaryl.

In summary, the present disclosure introduces a trifluoromethyl-containing reagent into an oxidative cleavage reaction. The reaction can use air or oxygen as an oxidant source under mild conditions, and the reaction is conducted using a proper catalyst to obtain a corresponding ketone or aldehyde. In addition, because of the introduction of the trifluoromethyl reagent, the other half of the oxidative cleavage reaction will be converted into trifluoromethyl or perfluoromethylketone, or trifluoromethyl aldehyde, perfluoroalkyl aldehyde, and trifluoromethyl or perfluroalkyl ethanol, which can be further used.

Other objects, advantages, and novel features of the invention will become more apparent from the following detailed description when taken in conjunction with the accompanying drawings.

DETAILED DESCRIPTION OF THE PREFERRED EMBODIMENT

Different embodiments of the present invention are provided in the following description. These embodiments are meant to explain the technical content of the present invention, but not meant to limit the scope of the present invention. A feature described in an embodiment may be applied to other embodiments by suitable modification, substitution, combination, or separation.

Preparation of an Unsaturated Double Bond with an Unsaturated Double Bond

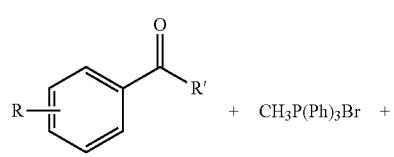

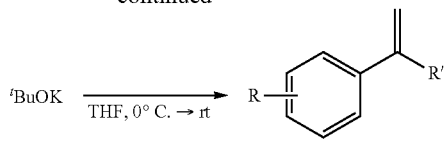

In a flame-dried, 50-mL, two-necked, round-bottomed flask was placed methyltriphenylphosphonium bromide (3.0 equiv) dissolved in 1 mL THF (0.2 M) at 0° C. Then added tert-BuOK (3.0 equiv) stirred at 0° C. After 30 minutes, add ketone or aldehyde (1.0 equiv) and let it warm to room temperature. After having been complete of the reaction, the reaction was quenched with $H_2O$ and extracted with EtOAc for three times. The combined organic layers dried over $MgSO_4$, and the filtrate was concentrated. The crude product was purified using flash column chromatography on silica gel with pure hexane as eluent to afford styrene derivatives.

1-nitro-4-(prop-1-en-2-yl)benzene

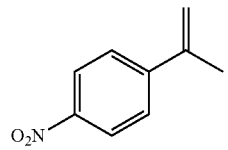

$^1$H NMR (CDCl$_3$, 400 MHz) δ 8.19 (d, J=9.0 Hz, 2H), 7.60 (d, J=9.1 Hz, 2H), 5.52 (t, J=0.8 Hz, 1H), 5.29 (t, J=1.3 Hz, 1H), 2.19 (dd, J=1.5, 0.8 Hz, 3H); $^{13}$C NMR (CDCl$_3$, 100 MHz) δ 147.6, 147.0, 141.6, 126.2, 123.6, 116.4, 21.6; TLC $R_f$ 0.47 (hexane); HRMS (FI) Calcd for $C_9H_9NO_2$: 163.0628, found: 163.0628.

4-(prop-1-en-2-yl)phenyl acetate

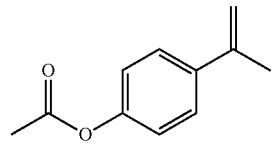

$^1$H NMR (CDCl$_3$, 500 MHz) δ 7.47 (d, J=9.0 Hz, 2H), 7.05 (d, J=8.5 Hz, 2H), 5.34 (s, 1H), 5.08 (s, 1H), 2.30 (s, 3H), 2.14 (s, 3H); $^{13}$C NMR (CDCl$_3$, 100 MHz) δ169.5, 150.0, 142.4, 140.0, 126.5, 121.2, 112.6, 21.8, 21.1; TLC $R_f$ 0.38 (hexane); HRMS (FI) Calcd for $C_{11}H_{12}O_2$: 176.0832, found: 176.0828.

1-methoxy-4-(prop-1-en-2-yl)benzene

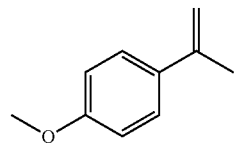

¹H NMR (CDCl₃, 400 MHz) δ7.43 (d, J=8.9 Hz, 2H), 6.87 (d, J=8.9 Hz, 2H), 5.29 (dq, J=1.6, 0.7 Hz, 1H), 4.99 (quin, J=1.5 Hz, 1H), 2.13 (t, J=0.9 Hz, 3H), 3.82 (s, 3H); ¹³C NMR (CDCl₃, 100 MHz) δ 159.0, 142.5, 133.7, 126.6, 113.5, 110.6, 55.3, 21.9; TLC R_f 0.42 (hexane); HRMS (FI) Calcd for C₁₀H₁₂O: 148.0883, found: 148.0887.

2-(prop-1-en-2-yl)naphthalene

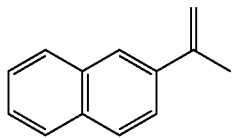

¹H NMR (400 MHz, CDCl₃) δ 7.87-7.82 (m, 4H), 7.71-7.68 (m, 1H), 7.51-7.44 (m, 2H), 5.56 (s, 1H), 5.22-5.21 (m, 1H), 2.29 (s, 3H); ¹³C NMR (100 MHz, CDCl₃) δ143.0, 138.3, 133.3, 132.8, 128.2, 127.7, 127.5, 126.1, 125.8, 124.2, 123.9, 113.0, 21.8; TLC R_f 0.49 (hexane); HRMS (FI) Calcd for C₃H₁₀: 168.0934, found: 168.0928.

4-(prop-1-en-2-yl)pyridine

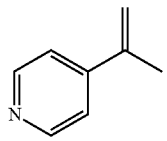

¹H NMR (CDCl₃, 400 MHz) δ 8.55 (d, J=6 Hz, 2H), 7.33 (d, J=5.2 Hz, 2H), 5.57 (d, J=0.6 Hz, 1H), 5.26 (d, J 1.0 Hz, 2H), 2.14 (s, 3H); ¹³C NMR (CDCl₃, 100 MHz) δ 150.7, 149.4, 148.2, 140.7, 121.0, 119.9, 115.8, 20.6; TLC R_f 0.30 (EtOAc/Hexane=1/5); HRMS (FI) Calcd for C₈H₉N: 119.0730, found: 119.0730.

2-(prop-1-en-2-yl)pyridine

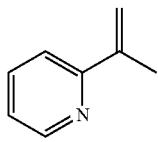

¹H NMR (CDCl₃, 400 MHz) 8.68 (td, J=4, 0.8 Hz, 1H), 8.03 (dd, J=8.0, 0.8 Hz, 1H), 7.82 (dt, J=7.8, 1.6 Hz, 1H), 7.44-7.48 (m, 1H), 2.72 (s, 3H); ¹³C NMR (CDCl₃, 100 MHz) δ 199.4, 153.1, 148.6, 136.4, 136.1, 126.7, 121.1, 25.3; TLC R_f 0.25 (EtOAc/Hexane=1/5); HRMS (FI) Calcd for C₈H₉N: 119.0730, found: 119.0729.

2-(prop-1-en-2-yl)thiophene

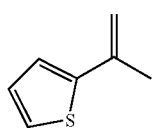

¹H NMR (400 MHz, CDCl₃) δ7.15 (dd, J=5.1, 1.1 Hz, 1H), 7.02 (dd, J=3.6, 1.1 Hz, 1H), 6.96 (dd, J=5.1, 3.6 Hz, 1H), 5.37 (s, 1H), 4.94 (m, 1H), 2.14 (m, 3H); ¹³C NMR (125 MHz, CDCl₃) δ145.8, 137.1, 127.2, 124.2, 123.5, 111.1, 21.8; TLC R_f 0.43 (hexane); HRMS (FI) Calcd for C₇H₈S: 124.0341, found: 124.0340.

Prop-1-en-2-ylcyclohexane

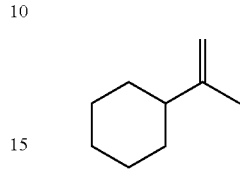

¹H NMR (CDCl₃, 400 MHz) δ 4.66 (s, 2H), 1.90-1.82 (m, 2H), 1.78-1.1.71 (m, 7H), 1.30-1.11 (m, 6H); ¹³C NMR (CDCl₃, 100 MHz) δ 151.3, 107.8, 45.5, 32.0, 26.8, 26.4, 20.9; TLC R_f 0.6 (hexane); HRMS (FI) Calcd for C₉H₁₆: 124.1247, found: 124.1243.

3-bromoprop-1-en-2-yl)benzene

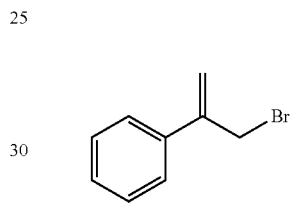

¹H NMR (CDCl₃, 400 MHz) δ 7.51-7.34 (m, 5H), 5.57 (s, 1H), 5.50 (s, 1H), 4.40 (s, 2H); ¹³C NMR (CDCl₃, 100 MHz) δ 144.2, 137.6, 128.5, 128.3, 126.1, 117.2, 34.2; TLC R_f 0.51 (hexane); HRMS (EI) Calcd for C₉H₉Br: 195.9882, found: 195.9882.

(1-cyclopropylvinyl)benzene

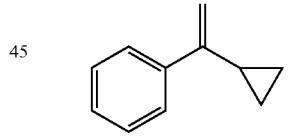

¹H NMR (CDCl₃, 400 MHz) δ 7.62-7.59 (m, 2H), 7.37-7.26 (m, 3H), 5.28 (s, 1H), 4.94 (s, 1H), 1.68-1.64 (m, 1H), 0.87-0.82 (m, 2H), 0.61-0.58 (m, 2H); ¹³C NMR (CDCl₃, 100 MHz) δ149.4, 141.6, 128.1, 127.4, 126.1, 109.0, 15.6, 6.7; TLC R_f 0.48 (hexane); HRMS (F) Calcd for C₁₁H₁₂: 144.0934, found: 144.0936.

(1-cyclohexylvinyl)benzene

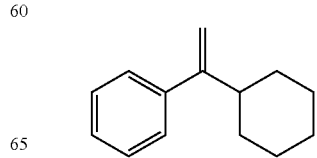

$^1$H NMR (CDCl$_3$, 400 MHz) δ 7.36-7.25 (m, 5H), 5.14 (s, 1H), 5.01 (s, 1H), 2.43 (t, J=11.6 Hz, 1H), 1.86-1.70 (m, 5H), 1.38-1.13 (m, 5H); $^{13}$C NMR (CDCl$_3$, 100 MHz) δ 154.99, 142.97, 128.10, 126.97, 126.62, 110.31, 42.58, 32.71, 26.84, 26.45; TLC R$_f$ 0.5 (hexane); HRMS (FI) Calcd for C$_{14}$H$_{18}$: 186.1403, found: 186.1402.

(3,3-dimethylbut-1-en-2-yl)benzene

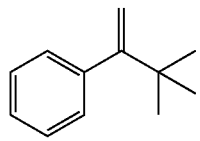

$^1$H NMR (CDCl$_3$, 400 MHz) δ 7.31-7.26 (m, 3H), 7.16-7.14 (m, 2H), 5.18 (d, J=2.0 Hz, 1H), 4.77 (d, J=1.6 Hz, 1H), 1.13 (s, 9H); $^{13}$C NMR (CDCl$_3$, 100 MHz) δ 159.8, 143.5, 129.0, 127.2, 126.2, 111.5, 36.1, 29.6; TLC R$_f$ 0.4 (hexane); HRMS (FI) Calcd for C$_{12}$H$_{16}$: 160.1247, found: 160.1247.

1-methylene-2,3-dihydro-1H-indene

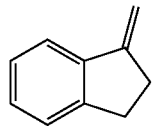

$^1$H NMR (CDCl$_3$, 400 MHz) δ7.52-7.50 (m, 1H), 7.28-7.20 (m, 3H), 5.46 (t, J=2.4 Hz, 1H), 5.04 (t, J=2.4 Hz, 1H), 3.01-2.98 (m, 2H), 2.83-2.78 (m, 2H); $^{13}$C NMR (CDCl$_3$, 125 MHz) δ150.6, 146.7, 141.1, 128.2, 126.4, 125.3, 120.6, 102.4, 31.2, 30.1; TLC R$_f$ 0.5 (hexane); HRMS (FI) Calcd for C$_{10}$H$_{10}$: 130.0777, found: 130.0776.

Synthesis of Catalyst (II)-1

In the present embodiment, the catalyst can be synthesized according to the following chemical equation.

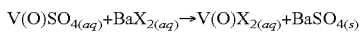

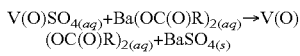

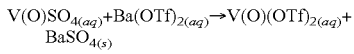

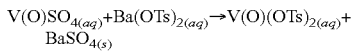

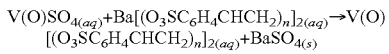

In a flame-dried, 50-mL, two-necked, round-bottomed flask was placed vanadyl sulfate-VOSO$_4$·5H$_2$O (VOSO$_4$.5H$_2$O, 2.5 mmol) followed by addition of anhydrous MeOH (2.5 mL). To the above solution, a solution of Ba(OTf)$_2$ (1 equiv, 2.5 mmol) in MeOH (2.5 mL) was slowly added at ambient temperature. After stirring for 30 minutes, the reaction mixture became turbid with copious amount of barium sulfate precipitation. Centrifugation (6000 rpm) for the mixture was performed for 30 minutes. The decanted solution was evaporated to give a dark green or faint blue solid which was further dried at 120° C. for 4 hours in vacuo. The resultant catalyst can be stored at ambient temperature for several weeks in dry cabinet and can be used directly.

Synthesis of catalyst (II)-2

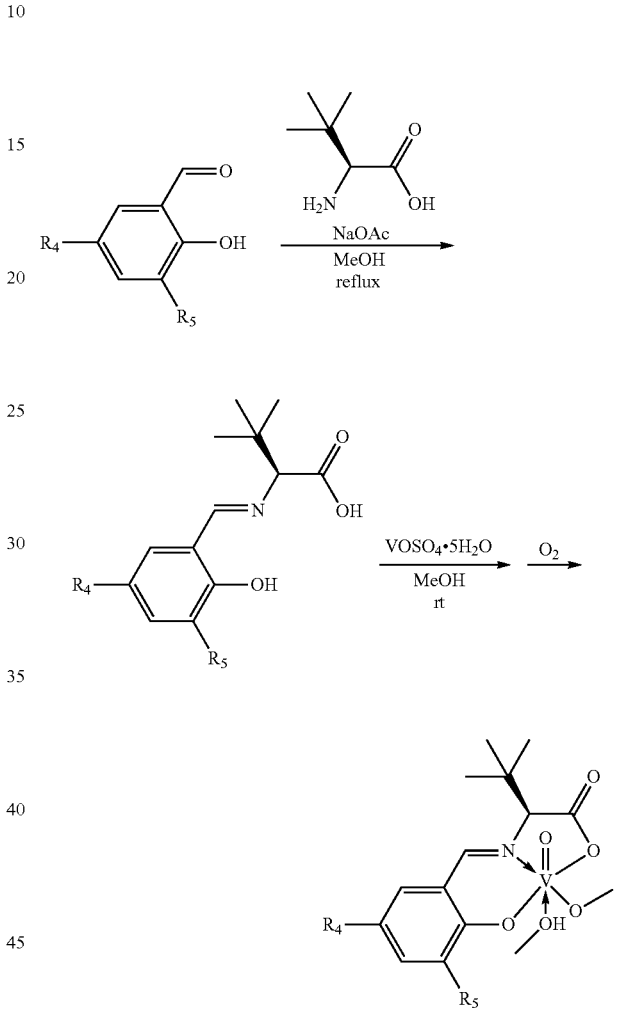

To the solution of 3,5-di-tert-butyl-2-hydroxybenzaldehyde (1217 mg, 5.0 mmol, 1.0 equiv) in MeOH (12.5 mL) was added L-tert-leucine (721 mg, 5.5 mmol, 1.1 equiv) or other 18 natural L-α-amino acids (721 mg, 5.5 mmol, 1.1 equiv) and NaOAc (902 mg, 11.0 mmol, 2.2 equiv). After stirring at 80° C. for 18 hours, the reaction mixture was gradually cooled to ambient temperature and a solution of VOSO$_4$.5H$_2$O (1392 mg, 5.5 mmol, 1.1 equiv) in MeOH (5.0 mL) was added. After the reaction was performed at ambient temperature for 6 hours, the reaction mixture was concentrated under reduced pressure. The resulting dark black solid was washed with water (5×30 mL) and dried in vacuo to afford a pure oxidovanadium(IV) catalyst. The corresponding analytically pure oxidovanadium(V) methoxide (or hydroxide) complex (11-1) was obtained by recrystallization from oxygen saturated MeOH.

Catalyst (II-1)

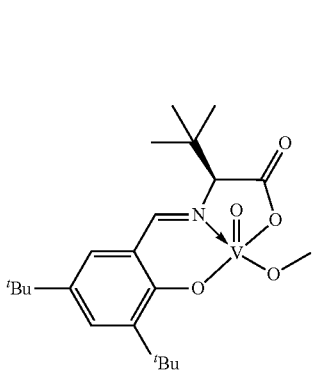

Yield: 84%; black solid. $^1$H NMR (CD$_3$OD, 500 MHz) δ 8.60 (bs, 1H), 7.68 (d, J=2.2 Hz, 1H), 7.48 (d, J=2.3 Hz, 1H), 4.14 (s, 1H), 1.47 (s, 9H), 1.35 (s, 9H), 1.21 (s, 9H); $^{51}$V NMR (CD$_3$OD, 132 MHz) δ −565.0; $^{13}$C NMR (CD$_3$OD, 126 MHz) δ 180.1, 168.9, 161.7, 143.5, 138.6, 132.4, 129.5, 129.4, 121.9, 84.7, 49.6, 49.3, 49.2, 49.0, 48.8, 48.6, 48.4, 38.3, 36.3, 35.3, 31.8, 30.3, 28.1; IR (KBr) 3370 (br, w), 2959 (w), 2871 (w), 1698 (m), 1668 (m), 1620 (s, C=N), 1580 (w), 1524 (m, COO), 1480 (w), 1456 (w), 1373 (w), 1322 (w), 1285 (w), 1182 (w), 1071 (w), 986 (m, V=O); $[α]_D^{34}$ +36.53 (c 0.1, CH$_2$Cl$_2$); TLC R$_f$ 0.37 (CH$_3$OH/CH$_2$Cl$_2$, 1/8); HRMS (ESI) [M+H]$^+$ Calcd for C$_{22}$H$_{34}$NO$_5$V: 444.1959, found: 444.1949.

Catalyst (II-2)

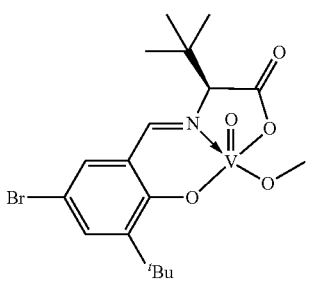

Yield: 57%; black solid. $^1$H NMR (CD$_3$OD, 400 MHz) δ 8.54 (bs, 1H), 7.66 (d, J=2.4 Hz, 1H), 7.62 (d, J=2.4 Hz, 1H), 4.15 (s, 1H), 3.33 (s, OCH$_3$), 1.44 (s, 9H), 1.18 (s, 9H); $^{51}$V NMR (CD$_3$OD, 105 MHz) δ −567.6; $^{13}$C NMR (CD$_3$OD, 126 MHz) δ 167.7, 142.3, 136.9, 136.2, 135.0, 134.6, 123.7, 111.9, 84.7, 49.8, 38.3, 37.2, 36.2, 29.9, 28.0, 27.4; IR (KBr) 2965 (s), 2913 (m), 2869 (m), 1663 (s), 1615 (s, C=N), 1578 (m), 1548 (m, COO), 1480 (w), 1429 (m), 1368 (m), 1320 (m), 1297 (s), 1181 (m), 1055 (w), 1031 (m), 993 (m, V=O); $[α]_D^{34}$ −126.4 (c 0.1, CH$_3$OH); TLC R$_f$ 0.20 (CH$_3$OH/CH$_2$Cl$_2$, 1/9); HRMS (ESI) [M+H]$^+$ Calcd for C$_{18}$H$_{25}$BrNO$_5$V: 466.0427; found: 466.0428.

Catalyst (II-3)

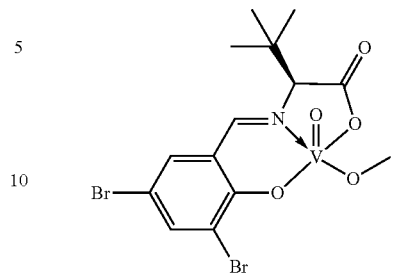

Yield: 75%; black solid. $^1$H NMR (CD$_3$OD, 400 MHz) δ 8.56 (bs, 1H), 7.96 (d, J=2.3 Hz, 1H), 7.78 (d, J=2.3 Hz, 1H), 4.18 (s, 1H), 1.20 (s, 9H); $^{51}$V NMR (CD$_3$OD, 105 MHz) δ −557.0; $^{13}$C NMR (CD$_3$OD, 126 MHz) δ 179.1, 167.2, 159.6, 141.7, 136.7, 123.6, 114.8, 110.9, 84.8, 49.9, 38.2, 28.1, 36.2, 29.9, 28.0, 27.4; IR (KBr) 3370 (br, w), 2959 (w), 2871 (w), 1698 (m), 1668 (m), 1620 (s, C=N), 1580 (w), 1524 (m, COO), 1480 (w), 1456 (w), 1373 (w), 1322 (w), 1285 (w), 1182 (w), 1071 (w), 986 (m, V=O); $[α]_D^{34}$ −40.8 (c 0.1, CH$_2$Cl$_2$); TLC R$_f$ 0.12 (CH$_3$OH/CH$_2$Cl$_2$, 1/10); HRMS (ESI) [M+H]$^+$ Calcd for C$_{14}$H$_{16}$Br$_2$NO$_5$V: 489.8880, found: 489.8888.

Catalyst (II-4)

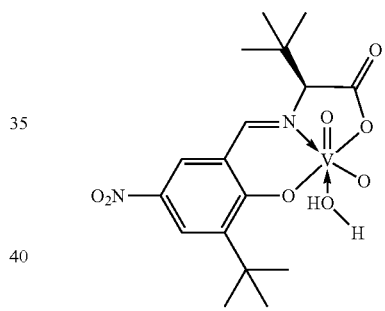

Yield: 81%; black solid. $^1$H NMR (CD$_3$OD, 400 MHz) δ 8.71 (bs, 1H), 8.54 (d, J=2.6 Hz, 1H), 8.39 (d, J=2.5 Hz, 1H), 4.24 (s, 1H), 3.31 (s, OCH$_3$), 1.49 (s, 9H), 1.22 (s, 9H); $^{51}$V NMR (CD$_3$OD, 105 MHz) δ 549.8, −568.8; $^{13}$C NMR (CD$_3$OD, 126 MHz) δ 168.0, 140.5, 139.1, 130.1, 130.0, 128.4, 127.6, 121.5, 84.9, 38.3, 36.5, 29.7, 28.0; IR (KBr) 2965 (w), 2916 (w), 2879 (w), 1627 (m, C=N), 1598 (m, COO), 1509 (w), 1326 (m), 1326 (w), 1225 (w), 1187 (w), 1113 (w), 1034 (w), 990 (w), 927 (w, V=O); MS (ESI) 850 (M$_2$O+H$_2$O, 90), 419 (MOH+H+, 9), 417 (MOH−1$^+$, 100); $[α]_D^{34}$ 83.93 (c 0.1, CH$_3$OH); TLC R$_f$ 0.30 (CH$_3$OH/CH$_2$Cl$_2$, 1/4); Anal. Calcd. For [(H$_2$O)MOH]: C, 46.80; H, 5.78; N, 6.42. Found: C, 45.57; H, 5.83; N, 6.15.

Oxidative Cleavage

[Reaction Scheme A]

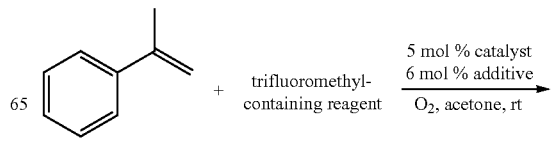

-continued

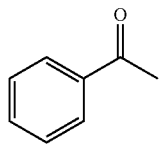

In a flame-dried, 50-mL, two-necked, round-bottomed flask was placed 5 mol % VO(OTf)$_2$. 5H$_2$O (11.8 mg, 0.025 mmol, 0.05 equiv) and 6 mol % additive (21.5 mg, 0.030 mmol, 0.06 equiv) and trifluoromethyl- or perfluoromethyl-containing reagent (346.6 mg, 1.05 mmol, 1.5 equiv) dissolved in 2.5 mL acetone. Then, α-methylstyrene (65 μL, 0.70 mmol, 1.0 equiv) was added. After having the reaction finished, the solvent was removed in vacuo, and the crude product was purified by using flash column chromatography on silica gel (ethyl acetate/hexane=1/8) to afford the product. The result is shown in Table 1.

TABLE 1

| Embodiment | Catalyst | Trifluoromethyl-containing reagent | Additive | Time (h) | Yield (%) |
|---|---|---|---|---|---|
| A-1 | Cu(CH$_3$CN)$_4$PF$_6$ | 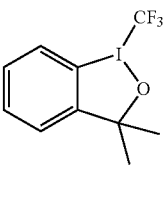 | 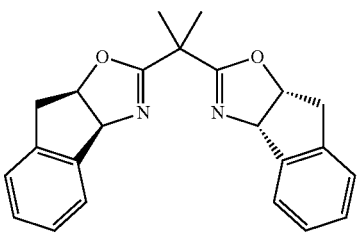 [SMILES: CC(C)(C1=N[C@H]2c3ccccc3C[C@H]2O1)C1=N[C@H]2c3ccccc3C[C@H]2O1] | 36 | 28 |
| A-2 | VO(OTf)$_2$•5H$_2$O | 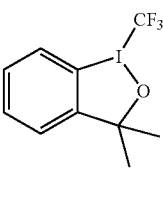 | 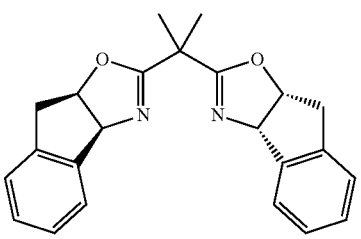 [SMILES: CC(C)(C1=N[C@H]2c3ccccc3C[C@H]2O1)C1=N[C@H]2c3ccccc3C[C@H]2O1] | 48 | 56 |
| A-3 | VO(OTf)$_2$•5H$_2$O | CF$_3$SO$_2$Na (1.2 eq) | 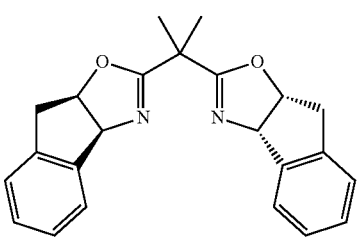 [SMILES: CC(C)(C1=N[C@H]2c3ccccc3C[C@H]2O1)C1=N[C@H]2c3ccccc3C[C@H]2O1] | 96 | 80 |
| A-4 | II-1 | 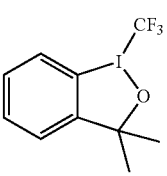 | — | 48 | 81 |
| A-5 | II-2 | 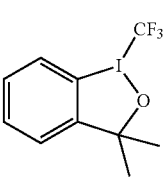 | — | 48 | 86 |
| A-6 | II-3 | 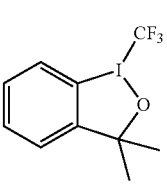 | — | 46 | 97 |

TABLE 1-continued

| Embodiment | Catalyst | Trifluoromethyl-containing reagent | Additive | Time (h) | Yield (%) |
|---|---|---|---|---|---|
| A-7 | II-4 | 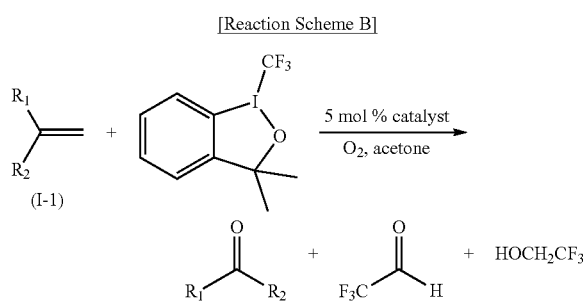 | — | 46 | 82 |

It can be found in Table 1 that the yield is low (28%) when the oxidative cleavage was performed with commercial catalyst $Cu(CH_3CN)_4PF_6$. The yield can be doubled or tripled when the catalyst $V(O)(OTf)_2$ was used in the reaction. When the reaction was performed with the catalyst of Formula (II-1) to Formula (II-4), the yield (81-97%) is significantly improved.

[Reaction Scheme B]

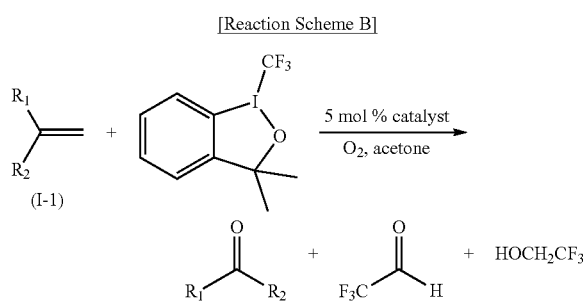

In aflame-dried, 25-mL, two-necked, round-bottomed flask was placed 5 mol % catalyst (eq II-3) and trifluoromethyl- or perfluoromethyl-containing reagent (1.5 equiv) dissolved in acetone (I mL). Then, a compound (1-1) (1.0 equiv) with an unsaturated double bond was added. After having the reaction finished, the solvent was removed in vacuo, and the crude product was purified by using flash column chromatography on silica gel (ethyl acetate/hexane=1/8) to afford the product. The result is shown in Table 2.

TABLE 2

| Embodiment | $R_1$ | $R_2$ | Time (h) | Yield (%) |
|---|---|---|---|---|
| B-1 | $C_6H_5$ | $CH_3$ | 46 | 97 |
| B-2 | $4\text{-}MeC_6H_4$ | $CH_3$ | 46 | 96 |
| B-3 | $4\text{-}PhC_6H_4$ | $CH_3$ | 48 | 90 |
| B-4 | $4\text{-}ClC_6H_4$ | $CH_3$ | 47 | 95 |
| B-5 | $4\text{-}BrC_6H_4$ | $CH_3$ | 47 | 93 |
| B-6 | $4\text{-}NO_2C_6H_4$ | $CH_3$ | 144 | 96 |
| B-7 | $4\text{-}CH_3CO_2C_6H_4$ | $CH_3$ | 72 | 92 |
| B-8 | $4\text{-}MeOC_6H_4$ | $CH_3$ | 84 | 95 |
| B-9 | $3\text{-}MeC_6H_4$ | $CH_3$ | 47 | 91 |
| B-10 | $2\text{-}MeC_6H_4$ | $CH_3$ | 46 | 93 |
| B-11 | 2-Naphthyl | $CH_3$ | 46 | 90 |
| B-12 | 4-Py | $CH_3$ | 120 | 92 |
| B-13 | 2-Py | $CH_3$ | 144 | 90 |
| B-14 | 2-Th | $CH_3$ | 45 | 93 |
| B-15 | cyclohexyl | $CH_3$ | 50 | 92 |

With the catalyst of Formula (II-3) of the present disclosure, the oxidative cleavage is carried out without adding additives. The resultant product with high isolated yield (90-97%) can be obtained in the aromatic system, and the reaction time is 46 to 144 hours. Also, the resultant product with high isolated yield (90-93%) can be obtained in the heteroaryl system, and the reaction time is 45 to 144 hours. The isolated yield is up to 92% in the cycloalkyl system, and the reaction time is 50 hours.

In addition, through $^{19}F$ NMR spectroscopic analysis, it is found that the other half of the main oxidative cleavage is converted to trifluoromethylketone or trifluoroaldehyde and trifluoroethanol (or the corresponding trifluoromethyl alcohol) rather than formaldehyde or 1,3,5-trioxane after the oxidative cleavage.

[Reaction Scheme C]

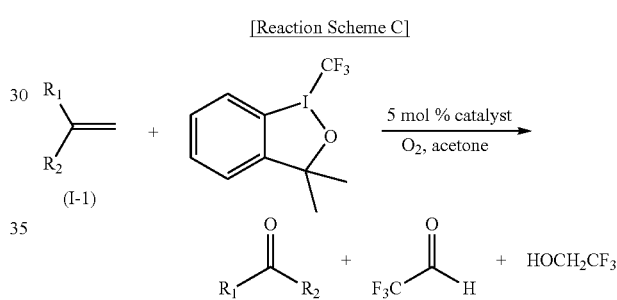

The reaction was performed in the same manner as described above, and the result is shown in Table 3.

TABLE 3

| Embodiment | $R_1$ | $R_2$ | Time (h) | Yield (%) |
|---|---|---|---|---|
| C-1 | $C_6H_5$ | $CH_2Br$ | 193 | 91 |
| C-2 | $C_6H_5$ | cy-Pr | 90 | 89 |
| C-3 | $C_6H_5$ | cy-hex | 96 | 95 |
| C-4 | $C_6H_5$ | t-Bu | 192 | 92 |
| C-5 | $C_6H_5$ | Ph | 48 | 95 |
| C-6 | | | 45 | 95 |

It was found that if $R_1$ of the compound (I) with an unsaturated double bond was designated as phenyl to perform the oxidative cleavage reaction, the isolated yield was 91-92% with a longer reaction time (192-193 hours) when $R_2$ was an alkyl system. When $R_2$ was a cycloalkyl system, the yield is 89-95%, and the reaction time was shortened to 90-96 hours. In addition, when $R_2$ is aryl or $R_1$ and $R_2$ are fused to be an aralkyl system, the yield is up to 95%, and the reaction time is significantly reduced to 45-48 hours.

[Reaction Scheme D]

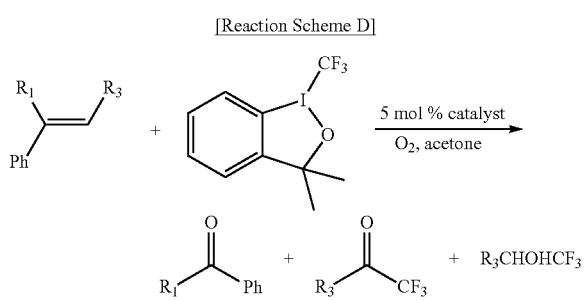

The reaction was performed in the same manner as described above, and the result is shown in Table 4.

TABLE 4

| Embodiment | $R_1$ | $R_3$ | Time (h) | Yield (%) |
|---|---|---|---|---|
| D-1 | H | $CH_3$ | 96 | 60 |
| D-2 | $CH_3$ | $CH_3$ | 96 | 82[a] |

[a] the reaction was performed at 50° C.

[Reaction Scheme E]

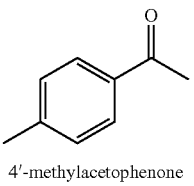

The reaction was performed in the same manner as described above, and the result is shown in Table 5.

TABLE 5

| Embodiment | Ar | Time (h) | Yield (%) |
|---|---|---|---|
| E-1 | 4-$XC_6H_4$[b] | 17-24 | 38-40 |
| E-2 | 4-$CH_3CO_2C_6H_4$ | 26 | 41 |
| E-3 | 4-Me or 4-$PhC_6H_4$ | 18-19 | 41-43 |
| E-4 | 3-$ClC_6H_4$ | 96 | 62 |
| E-5 | 2-$XC_6H_4$[b] | 20-26 | 58-65 |

[b] X is halogen (F, Cl, Br, I)

When the $R_2$ and $R_3$ of the compound (I) with an unsaturated double bond is H, the corresponding benzaldehyde, trifluoroaldehyde and trifluoroethanol can be obtained.

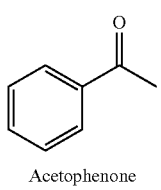

Acetophenone $^1$H NMR (CDCl$_3$, 400 MHz) δ 7.97-7.95 (m, 2H), 7.58-7.54 (m, 1H), 7.84-7.44 (m, 2H), 2.6 (s, 3H); $^{13}$C NMR (CDCl$_3$, 125 MHz) δ 198.0, 137.0, 133.0, 128.4, 128.2, 26.4; TLC R$_f$ 0.32 (EtOAc/Hexane=1/15); HRMS (FI) Calcd for C$_8$H$_8$O: 120.0570, found: 120.0569.

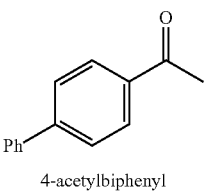

4'-methylacetophenone $^1$H NMR (CDCl$_3$, 400 MHz) δ 7.86-7.85 (m, 2H), 7.26 (d, J=7.6 Hz, 2H), 2.58 (s, 3H), 2.41 (s, 3H); $^{13}$C NMR (CDCl$_3$, 125 MHz) δ 197.8, 143.9, 134.7, 129.2, 128.4, 26.5, 21.60; TLC R$_f$ 0.25 (EtOAc/Hexane=1/15); HRMS (FI) Calcd for C$_9$H$_{10}$O: 134.0726, found: 134.0725.

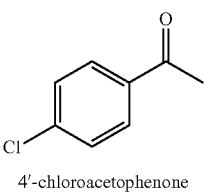

4-acetylbiphenyl $^1$H NMR (CDCl$_3$, 400 MHz) δ 8.05-8.02 (m, 2H), 7.71-7.68 (m, 2H), 7.65-7.62 (m, 2H), 7.50-7.45 (m, 2H), 7.43-7.38 (m, 2H), 2.65 (s, 3H); $^{13}$C NMR (CDCl$_3$, 125 MHz) δ197.7, 145.8, 139.9, 135.9, 128.9, 128.9, 128.2, 127.3, 127.2, 26.6; TLC R$_f$0.3 (EtOAc/Hexane=1/10); HRMS (FI) Calcd for C$_{14}$H$_{12}$O: 196.0883, found: 196.0822.

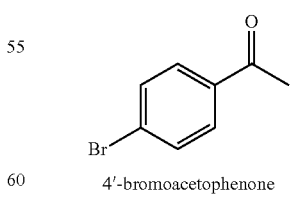

4'-chloroacetophenone $^1$H NMR (CDCl$_3$, 400 MHz) δ 7.91-7.87 (m, 2H), 7.45-7.41 (m, 2H), 2.59 (s, 3H); $^{13}$C NMR (CDCl$_3$, 125 MHz) δ 196.7, 139.5, 135.4, 129.6, 128.8, 26.4; TLC R$_f$ 0.23 (EtOAc/Hexane=1/20); HRMS (FI) Calcd for C$_8$H$_7$ClO: 154.0180, found: 154.0181.

4'-bromoacetophenone $^1$H NMR (CDCl$_3$, 400 MHz) δ 7.84-7.81 (m, 2H), 7.62-7.60 (m, 2H), 2.59 (s, 3H); $^{13}$C NMR (CDCl$_3$, 125 MHz) δ 196.9, 135.8, 131.9, 129.8, 128.3, 26.5; TLC R$_f$ 0.28 (EtOAc/Hexane=1/15); HRMS (FI) Calcd for C$_8$H$_7$BrO: 197.9675, found: 197.9676.

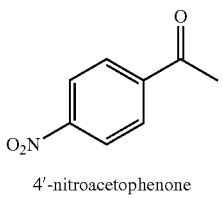

4'-nitroacetophenone

¹H NMR (CDCl₃, 400 MHz) δ 8.33-8.29 (m, 2H), 8.12-8.09 (m, 2H), 2.68 (s, 3H); ¹³C NMR (CDCl₃, 125 MHz) δ 196.2, 150.4, 141.4, 129.3, 123.8, 26.9; TLC $R_f$ 0.35 (EtOAc/Hexane=1/5); HRMS (FI) Calcd for C₈H₇NO₃: 165.0420, found: 165.0421.

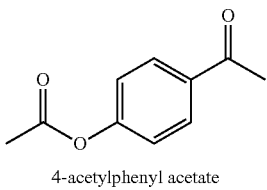

4-acetylphenyl acetate

¹H NMR (CDCl₃, 400 MHz) δ 8.00-7.97 (m, 2H), 7.20-7.16 (m, 2H), 2.58 (s, 3H), 2.31 (s, 3H); ¹³C NMR (CDCl₃, 125 MHz) δ 196.8, 168.8, 154.3, 134.7, 129.9, 121.7, 26.5, 21.1; TLC $R_f$ 0.30 (EtOAc/Hexane=1/5); HRMS (FI) Calcd for C₁₀H₁₀O₃: 178.0624, found: 178.0625.

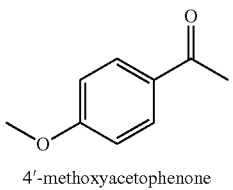

4'-methoxyacetophenone

¹H NMR (CDCl₃, 400 MHz) δ 7.95-7.92 (m, 2H), 6.95-6.91 (m, 2H), 3.87 (s, 3H), 2.55 (s, 3H); ¹³C NMR (CDCl₃, 125 MHz) δ 196.7, 163.5, 130.6, 130.4, 113.7, 55.4, 26.3; TLC $R_f$ 0.35 (EtOAc/Hexane=1/5); HRMS (FI) Calcd for C₉H₁₀O₂: 150.0675, found: 105.0676.

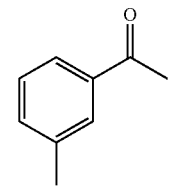

3'-methylacetophenone

¹H NMR (CDCl₃, 400 MHz) δ 7.77-7.37 (m, 2H), 7.39-7.26 (m, 2H), 2.59 (s, 3H), 2.41 (s, 3H); ¹³C NMR (CDCl₃, 125 MHz) δ 198.3, 138.3, 137.1, 133.8, 128.7, 128.4, 125.5, 26.5, 21.2; TLC $R_f$ 0.21 (EtOAc/Hexane=1/20); HRMS (FI) Calcd for C₉H₁₀O: 134.0726, found: 134.0724.

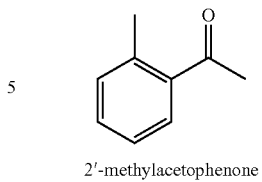

2'-methylacetophenone

¹H NMR (CDCl₃, 400 MHz) δ 7.71-7.68 (m, 1H), 7.40-7.36 (m, 1H), 7.29-7.24 (m, 2H), 2.58 (s, 3H), 2.53 (s, 3H); ¹³C NMR (CDCl₃, 125 MHz) δ 201.7, 138.3, 137.6, 132.0, 131.4, 129.3, 125.6, 29.5, 21.5; TLC $R_f$ 0.25 (EtOAc/Hexane=1/20); HRMS (FI) Calcd for C₉H₁₀O: 134.0726, found: 134.0724.

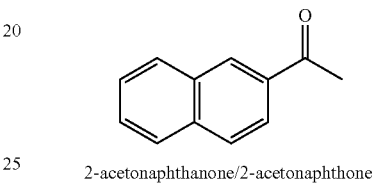

2-acetonaphthanone/2-acetonaphthone

¹H NMR (400 MHz, CDCl₃) δ 8.48 (s, 1H), 8.04 (dd, J=8.6, 1.4 Hz, 1H), 7.97 (d, J=8.0 Hz, 1H), 7.91-7.87 (m, 2H), 7.63-7.54 (m, 2H), 2.74 (s, 3H); ¹³C NMR (125 MHz, CDCl₃) δ 198.1, 135.6, 134.5, 132.5, 130.2, 129.5, 128.4, 128.4, 127.8, 126.7, 123.9, 26.7; TLC $R_f$ 0.20 (EtOAc/Hexane=1/20); HRMS (FI) Calcd for C₂H₁₀O: 170.0726; found: 170.0721.

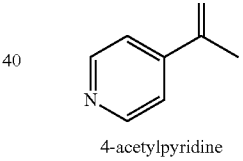

4-acetylpyridine

¹H NMR (CDCl₃, 400 MHz) δ 8.80 (dd, J=4.4, 1.6 Hz, 2H), 7.72 (dd, J=4.4, 1.6 Hz, 2H), 2.62 (s, 1H); ¹³C NMR (CDCl₃, 100 MHz) δ 196.6, 150.2, 142.0, 120.5, 25.9; TLC $R_f$ 0.20 (EtOAc/Hexane=1/3); HRMS (FI) Calcd for C₇H₇NO: 121.0522, found: 121.0522.

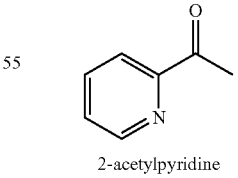

2-acetylpyridine

¹H NMR (CDCl₃, 400 MHz) δ 8.68 (td, J=4.0, 0.8 Hz, 1H), 8.03 (dd, J=8.0, 0.8 Hz, 1H), 7.82 (dt, J=7.8, 1.6 Hz, 1H), 7.44-7.48 (m, 1H), 2.72 (s, 3H); ¹³C NMR (CDCl₃, 100 MHz) δ 199.4, 153.1, 148.6, 136.4, 136.1, 126.7, 121.1, 25.3; TLC $R_f$ 0.25 (EtOAc/Hexane=1/5); HRMS (FI) Calcd for C₇H₇NO: 121.0522, found: 121.0521.

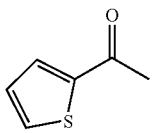

2-acetylthiophene

¹H NMR (400 MHz, CDCl$_3$) δ 7.70 (dd, J=3.5, 1.2 Hz, 2H), 7.64 (dd, J=4.9, 1.2 Hz, 1H), 7.13 (dd, J=4.9, 3.5 Hz, 2H), 2.57 (s, 3H); ¹³C NMR (125 MHz, CDCl$_3$) δ 190.6, 144.5, 133.7, 132.4, 128.0, 26.8; TLC R$_f$ 0.30 (EtOAc/Hexane=1/10); HRMS (FI) Calcd for C$_6$HOS: 126.0134, found: 126.0133.

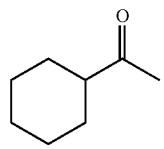

Cyclohexyl methyl ketone

¹H NMR (CDCl$_3$, 400 MHz) δ 2.34-2.30 (m, 1H), 2.11 (s, 3H), 2.19-1.84 (m, 2H), 1.79-1.74 (m, 2H), 1.67-1.63 (m, 1H), 1.33-1.19 (m, 5H); ¹³C NMR (CDCl$_3$, 100 MHz) δ 212.3, 51.4, 28.4, 27.8, 25.8, 25.6; TLC R$_f$ 0.21 (EtOAc/Hexane=1/15); HRMS (FI) Calcd for C$_8$H$_{14}$O: 126.1039, found: 126.1036.

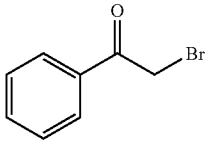

2-bromoacetophenone

¹H NMR (CDCl$_3$, 400 MHz) δ 8.00-7.98 (m, 2H), 7.64-7.60 (m, 1H), 7.52-7.50 (m, 2H), 4.46 (s, 2H); ¹³C NMR (CDCl$_3$, 125 MHz) δ 191.3, 134.0, 134.0, 128.9, 128.8, 30.9; TLC R$_f$ 0.25 (EtOAc/Hexane=1/20); HRMS (EI) Calcd for C$_8$H$_7$BrO: 197.9675, found: 197.9679.

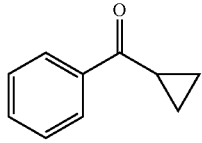

Cyclopropyl phenyl ketone

¹H NMR (CDCl$_3$, 400 MHz) δ 8.03-8.00 (m, 2H), 7.59-7.54 (m, 1H), 7.50-7.45 (m, 2H), 2.71-2.65 (m, 2H), 1.27-1.23 (m, 2H), 1.07-1.02 (m, 2H); ¹³C NMR (CDCl$_3$, 125 MHz) δ 200.5, 137.9, 132.6, 128.4, 127.9, 17.0, 11.5; TLC R$_f$ 0.20 (EtOAc/Hexane=1/15); HRMS (FI) Calcd for C$_{10}$H$_{10}$O: 146.0726, found: 146.0727.

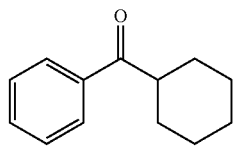

Cyclohexyl phenyl ketone

¹H NMR (CDCl$_3$, 400 MHz) δ 7.94 (d, J=7.2 Hz, 2H), 7.55 (tt, J=7.2, 2.0 Hz, 1H), 7.46 (t, J=7.4 Hz, 2H), 3.26 (tt, J=11.2, 3.2 Hz, 1H), 1.91-1.82 (m, 4H), 1.76-1.72 (m, 1H), 1.55-1.25 (m, 5H); ¹³C NMR (CDCl$_3$, 100 MHz) δ 203.9, 136.4, 132.7, 128.6, 128.3, 45.6, 29.4, 26.0, 25.9; TLC R$_f$ 0.3 (EtOAc/Hexane=1/10); HRMS (FI) Calcd for C$_{13}$H$_{16}$OF$_3$: 188.1196, found: 188.1195.

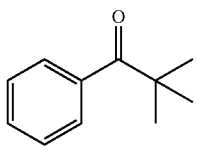

2,2-dimethylpropiophenone

¹H NMR (CDCl$_3$, 400 MHz) δ 7.70-7.67 (m, 2H), 7.47-7.37 (m, 3H), 1.35 (s, 9H); ¹³C NMR (CDCl$_3$, 125 MHz) δ 209.3, 138.6, 130.7, 128.0, 127.8, 44.2, 28.0; TLC R$_f$ 0.4 (EtOAc/Hexane=1/20); HRMS (FI) Calcd for C$_{11}$H$_{14}$O: 162.1039, found: 162.1038.

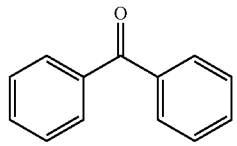

Benzophenone

¹H NMR (CDCl$_3$, 400 MHz) δ 7.82-7.80 (m, 4H), 7.62-7.57 (m, 2H), 7.51-7.47 (m, 4H); ¹³C NMR (CDCl$_3$, 125 MHz) δ 196.7, 137.5, 132.4, 123.0, 128.2; TLC R$_f$ 0.35 (EtOAc/Hexane=1/10); HRMS (FI) Calcd for C$_{13}$H$_{10}$O: 182.0726, found: 182.0725.

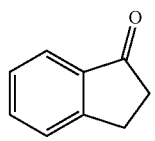

1-indanone

¹H NMR (CDCl$_3$, 400 MHz) δ 7.76 (d, J=7.2 Hz, 1H), 7.61-7.57 (m, 1H), 7.50-7.47 (m, 1H), 7.39-7.35 (m, 1H), 3.15 (t, J=6.0 Hz, 2H), 2.71-2.68 (m, 2H); ¹³C NMR (CDCl$_3$, 125 MHz) δ 206.9, 155.1, 137.0, 134.5, 127.2, 126.6, 123.6, 36.1, 25.7; TLC R$_f$ 0.3 (EtOAc/Hexane=1/10); HRMS (FI) Calcd for C$_9$H$_8$O: 132.0570, found: 132.0570.

CF$_3$CH$_2$OH (Trifluoroethanol): ¹H NMR (400 MHz, CDCl$_3$) δ 3.92 (q, J=8.8 Hz, 2H), 3.21 (br, 1H, OH); ¹⁹F NMR (470 MHz, CDCl$_3$) δ −79.08 (s).

CF$_3$CHO (Trifluoroacetaldehyde; b.p. −18° C.): ¹⁹F NMR (470 MHz, CDCl$_3$) δ −84.62 (s)

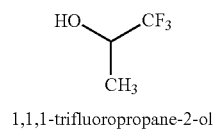

1,1,1-trifluoropropane-2-ol $^1$H NMR (CDCl$_3$, 500 MHz) δ 3.98 (sept, J=6.5 Hz, 1H), 3.17 (s, 1H, OH), 1.38 (d, J=6.5 Hz, 3H); $^{19}$F NMR (470 MHz, CDCl$_3$) δ −81.4 (s).

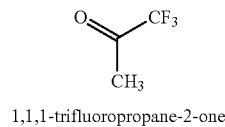

1,1,1-trifluoropropane-2-one $^1$H NMR (CDCl$_3$, 500 MHz) δ 2.48 (s, 3H); $^{19}$F NMR (470 MHz, CDCl$_3$) δ −80.0 (s).

Although the present invention has been explained in relation to its preferred embodiment, it is to be understood that many other possible modifications and variations can be made without departing from the spirit and scope of the invention as hereinafter claimed.

What is claimed is:

1. A method for oxidative cleavage of a compound with an unsaturated double bond, comprising the steps of:
   (A) providing a compound (I) with an unsaturated double bond, a trifluoromethyl-containing reagent, and a catalyst;

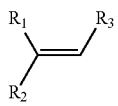 (I)

wherein, R$_1$ and R$_2$ are each independently H, C$_{1-20}$ alkyl, C$_{3-20}$ cycloalkyl, C$_{6-18}$ aryl, or C$_{4-18}$ heteroaryl, or R$_1$ and R$_2$ are fused to be C$_{6-18}$ aralkyl; R$_3$ is H, C$_{1-10}$ alkyl, C$_{3-10}$ cycloalkyl, C$_{6-10}$ aryl, or C$_{4-10}$ heteroaryl, with the proviso that R$_1$, R$_2$ and R$_3$ are not H at the same time;
wherein the catalyst is represented by Formula (II):

$$M(O)_m L^1_y L^2_z \quad (II)$$

wherein, M is a metal selected from the group consisting of IVB, VB, VIB, and actinides;
L$^1$ and L$^2$ are each a ligand;
m and y are integers greater than or equal to 1; and
z is an integer greater than or equal to 0;
(B) mixing the compound with the unsaturated double bond and the trifluoromethyl-containing reagent to perform an oxidative cleavage of the compound with the unsaturated double bond by using the catalyst in air or under oxygen atmosphere condition to obtain a compound represented by Formula (III):

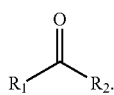 (III)

2. The method of claim 1, wherein R$_1$ and R$_2$ are each independently H, C$_{1-10}$ alkyl, C$_{3-10}$ cycloalkyl, C$_{6-14}$ aryl, or C$_{4-10}$ heteroaryl, or R$_1$ and R$_2$ are fused to be C$_{6-12}$ aralkyl; R$_3$ is H, C$_{1-6}$ alkyl, C$_{3-6}$ cycloalkyl, C$_{6-10}$ aryl, or C$_{4-10}$ heteroaryl.

3. The method of claim 1, wherein L$^1$ is selected from the group consisting of OTf, OTs, NTf$_2$, halogen, RC(O)CH$_2$C(O)R, OAc, OC(O)R, OC(O)CF$_3$, OMe, OEt, O-iPr, and butyl, wherein R is alkyl.

4. The method of claim 1, wherein L$^2$ is selected from the group consisting of Cl, H$_2$O, CH$_3$OH, EtOH, THF, CH$_3$CN,

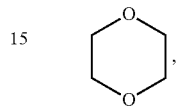

and ligand containing C=N unit.

5. The method of claim 4, wherein the ligand containing C=N unit comprises pyridine, oxazole, oxazoline, or imidazole.

6. The method of claim 5, wherein the ligand containing C=N unit is represented by Formula (V):

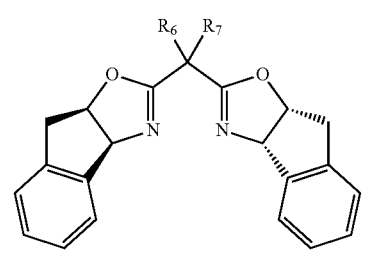 (V)

wherein R$_6$ and R$_7$ are each independently H, C$_{1-5}$ alkyl or C$_{3-6}$ cycloalkyl.

7. The method of claim 4, wherein the ligand containing C=N unit is represented by Formula (IV):

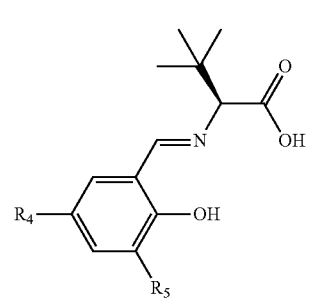 (IV)

wherein, R$_4$ and R$_5$ are each independently halogen, nitro, C$_{1-10}$ alkyl, C$_{6-18}$ aryl, or C$_{4-18}$ heteroaryl.

8. The method of claim 1, wherein the catalyst represented by Formula (II) is MoO$_2$Cl$_2$, V(O)Cl$_3$, V(O)(O-iPr)$_3$, V(O)Cl$_2$, V(O)(OAc)$_2$, V(O)(O$_2$CCF$_3$)$_2$, Ti(O)(acac)$_2$, Zr(O)Cl$_2$, Hf(O)Cl$_2$, Nb(O)Cl$_2$, MoO$_2$(acac)$_2$, V(O)(OTs)$_2$, VO(OTf)$_2$, or V(O)(NTf$_2$)$_2$.

9. The method of claim 1, wherein the catalyst represented by Formula (II) is any one of formulas (II-1) to (II-4):

(II-1)
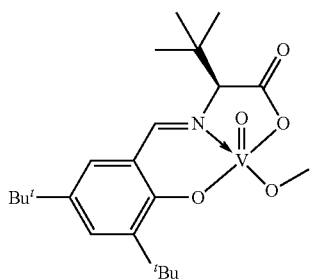

(II-2)
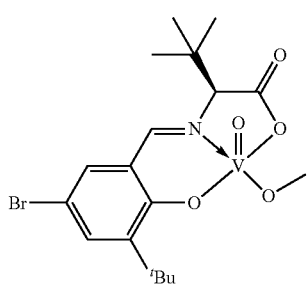

(II-3)
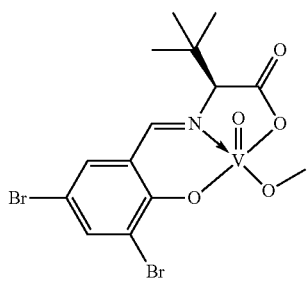

(II-4)
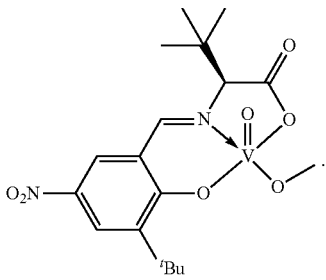

10. The method of claim 1, wherein the trifluoromethyl-containing reagent is 3,3-Dimethyl-1-(trifluoromethyl)-1,2-benziodoxole, 3,3-Dimethyl-1-(perfluroalkyl)-1,2-benziodoxole, 3-oxo-1-(trifluoromethyl)-1,2-benziodoxole, 3-oxo-1-(perfluroalkyl)-1,2-benziodoxole), trifluomethyl dibenzothiophenium salts, perfluoroalkyl dibenzothiophenium salts, $CF_3SO_2Na$, or $CF_3(CF_2)_nSO_2Na$, wherein n is an integer of 1 to 6.

11. The method of claim 1, wherein step (B) further obtains a trifluoroketone- or trifluoroaldehyde-containing compound represented by the following formula (VI), trifluoroalkyl alcohol represented by the following formula (VII) or a combination thereof:

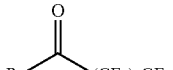 (VI)

$R_3CHOH(CF_2)_nCF_3$ (VII)

wherein $R_3$ is H, $C_{1-10}$ alkyl, $C_{3-10}$ cycloalkyl, $C_{6-10}$ aryl, or $C_{4-10}$ heteroaryl; n is an integer of 0 or 1 to 6.

* * * * *